United States Patent
Ishikubo et al.

(10) Patent No.: US 8,173,112 B2
(45) Date of Patent: May 8, 2012

(54) EMULSIFIED COMPOSITION FOR HAIR

(75) Inventors: Akira Ishikubo, Yokohama (JP);
Tomoyuki Kawasoe, Yokohama (JP);
Shunsuke Takeda, Yokohama (JP)

(73) Assignee: Shiseido Co., Ltd., Tokyo (JP)

( * ) Notice: Subject to any disclaimer, the term of this patent is extended or adjusted under 35 U.S.C. 154(b) by 1325 days.

(21) Appl. No.: 10/558,202

(22) PCT Filed: May 26, 2004

(86) PCT No.: PCT/JP2004/007532
§ 371 (c)(1),
(2), (4) Date: Jan. 18, 2007

(87) PCT Pub. No.: WO2004/103324
PCT Pub. Date: Dec. 2, 2004

(65) Prior Publication Data
US 2007/0274943 A1    Nov. 29, 2007

(30) Foreign Application Priority Data

May 26, 2003  (JP) ................................ 2003-147185
Sep. 17, 2003  (JP) ................................ 2003-324603

(51) Int. Cl.
*A61Q 5/00*    (2006.01)
(52) U.S. Cl. .................... 424/70.31; 424/70.1
(58) Field of Classification Search .......... None
See application file for complete search history.

(56) References Cited

U.S. PATENT DOCUMENTS

| 5,085,854 | A | * | 2/1992 | Fukuda et al. | 424/63 |
| 5,976,604 | A | * | 11/1999 | Kunieda et al. | 426/602 |
| 6,153,208 | A | * | 11/2000 | McAtee et al. | 424/402 |
| 6,528,071 | B2 | * | 3/2003 | Vatter et al. | 424/401 |
| 6,646,086 | B2 | * | 11/2003 | Slone | 526/319 |
| 7,297,717 | B2 | * | 11/2007 | Iwai et al. | 424/70.23 |
| 7,488,492 | B2 | * | 2/2009 | Furukawa et al. | 424/401 |

FOREIGN PATENT DOCUMENTS

| JP | 62-106837 | 5/1987 |
| JP | 8-127526 | 5/1996 |
| JP | 2711541 | 10/1997 |
| JP | 10-259114 | 9/1998 |
| JP | 2849339 | 11/1998 |
| JP | 11-171739 | 6/1999 |
| JP | 2002-138014 | 5/2002 |
| WO | WO 2004/103324 | 12/2004 |

* cited by examiner

*Primary Examiner* — Jyothsna Venkat
(74) *Attorney, Agent, or Firm* — Townsend & Banta

(57) ABSTRACT

An emulsified composition for hair, which contains a nonionic surfactant that is a solid at normal temperature and has a Krafft point of at least 40° C., an oil component, and water, and which has an average emulsified particle size of 0.5 μm or less, provides long-lasting luster. Further, an emulsified composition for hair, which is an water-in-oil emulsified composition and which contains the following two types of oil phase as the oil phase, improves the feel of hair immediately after use: 1) an oil phase with an average particle size of 0.5 μm or less, formed with a nonionic surfactant that is a solid at normal temperature and has a Krafft point of at least 40° C., and 2) an oil phase with an average particle size of 0.5 to 100 μm, formed with a surfactant and/or an alkyl-modified carboxyvinyl polymer.

1 Claim, No Drawings

EMULSIFIED COMPOSITION FOR HAIR

This application claims priority right to Japanese Patent Application 2003-147185 dated May 26, 2003, and Japanese Patent Application 2003-324603 dated Sep. 17, 2003, which are incorporated herein.

TECHNICAL FIELD

This invention relates to an emulsified composition used as a hair care product.

BACKGROUND ART

There have been many hair styling agents whose main purpose was to bring out the luster in hair, and most of these provided this luster by means of an oil component. Consequently, such hair styling agents are frequently emulsified compositions to which an oil component has been added, but while a base such as this does have an excellent effect on hair luster immediately after its use, over time the oil component can stick to and rub off on the fingers and other things, so the luster has a tendency to disappear.

In an effort to solve this problem, the present applicant has applied for a patent for a oil-in-water type of hair composition, in which a nonionic surfactant with a Krafft point of at least 40° C., such as a sucrose fatty acid ester, is used as a surfactant, and an oil phase component consisting of a micro-oil phase (emulsified particles) is slowly released. This emulsified composition for hair does afford excellent setting strength immediately after use, but also tends to make the hair feel stiff to the touch.

Prior publications related to the present invention are as follows.

Patent Document 1 (Japanese Patent 2,711,541) discusses an oil-in-polyhydric alcohol type of emulsified composition produced by adding an oil component to a gelled composition produced by mixing a sucrose fatty acid ester, a polyhydric alcohol, and water.

Patent Document 2 (Japanese Patent 2,849,339) discusses an emulsified cosmetic comprising an alkyl glycoside and a sucrose fatty acid ester contained in a cosmetic that contains an oil-based substance and water.

Patent Document 3 (Japanese Laid-Open Patent Application H11-171739) discusses a hair composition containing a special hair-treatment polymer and a sucrose fatty acid ester.

DISCLOSURE OF THE INVENTION

The present invention provides as a first invention a hair composition that provides long-lasting luster. It further provides as a second invention means for improving the feel immediately after the use of an emulsified hair composition containing micro-emulsified particles, using the above-mentioned sucrose fatty acid ester, etc.

As a result of research into the above problems, the inventors perfected the first invention of the present invention upon discovering that long-lasting luster can be imparted to hair by using as a hair cosmetic an emulsified composition containing micro-emulsified particles, using a specific surfactant, and limiting the oil component to a specific amount or less.

Specifically, the present invention provides an emulsified composition for hair (hereinafter also referred to as this emulsified composition) containing the following (a) to (c) and having an average emulsified particle size of 0.5 μm or less.

(a) a nonionic surfactant that is a solid at normal temperature and has a Krafft point of at least 40° C. (hereinafter also referred to as a specific surfactant)

(b) an oil component (contained in an amount of no more than 10 parts to 1 part (weight ratio) of the nonionic surfactant of (a))

(c) water

The Krafft point is the temperature at which the solubility of a surfactant in water increases sharply. It is known that below this temperature, the surfactant can only dissolve in monomolecular form, but above this temperature, the surfactant can dissolve in both monomolecular form and in micelle form (source: Kagaku Daijiten chemical Dictionary, Kyoritsu Publishing).

As a result of research into the above problems, the inventors perfected the second invention of the present invention upon discovering that if the above-mentioned micro-emulsified particles and other specific emulsified particles are both made to be present in an aqueous phase, the luster provided by the use of micro-emulsified particles will last longer, and the oil-in-water type of emulsified composition for hair that is obtained will be able to improve the feel of the hair immediately after use of the product.

Specifically, the present invention provides an emulsified composition for hair (hereinafter also referred to as this emulsified composition) which is an oil-in-water type of emulsified composition and which comprises the following two types of oil phase as the oil phase (d) an oil phase with an average particle size of 0.5 μm or less, formed with a nonionic surfactant that is a solid at normal temperature and has a Krafft point of at least 40° C.

(e) an oil phase with an average particle size of 0.5 to 100 μm, formed with a surfactant and/or an alkyl-modified carboxyvinyl polymer This emulsified composition is an oil-in-water type of emulsified composition in which the above-mentioned hard oil phase and soft oil phase are both present in the aqueous phase, and as long as these conditions are met, there are no restrictions on the method by which the emulsified composition is ultimately manufactured.

Typically, this emulsified composition can be manufactured by separately preparing an oil-in-water emulsified composition containing a hard oil phase (hereinafter also referred to as the first emulsified composition) and an emulsified composition containing a soft oil phase (hereinafter also referred to as the second emulsified composition), and then mixing these.

First Emulsified Composition

The first emulsified composition is an oil-in-water emulsified composition containing the following (a) to (c) and having an average emulsified particle size of 0.5 μm or less.

(a) a nonionic surfactant that is a solid at normal temperature and has a Krafft point of at least 40° C.

(b) an oil component (contained in an amount of no more than 10 parts to 1 part (weight ratio) of the nonionic surfactant of (a))

(c) water

The hard surfactant, which is a nonionic surfactant with a Krafft point or at least 40° C., is a nonionic surfactant whose solubility in water rises sharply at 40° C. or higher, but which precipitates as a solid when the surfactant aqueous solution returns to normal temperature after dissolution.

Specific favorable examples of hard surfactants include sucrose fatty acid esters (such as sucrose monostearic acid ester, sucrose monopalmitic acid ester, sucrose monolauric acid ester, sucrose monooleic acid ester, sucrose distearic acid ester, sucrose dipalmitic acid ester, sucrose dilauric acid ester, sucrose dioleic acid ester, and sucrose coconut oil fatty acid ester) and polyglycerol fatty acid esters (such as polyglycerol monostearic acid ester and polyglycerol monooleic acid ester).

BEST MODE FOR CARRYING OUT THE INVENTION

First Invention

As discussed above, the specific surfactant is a nonionic surfactant whose Krafft point is at least 40° C., or more specifically, a nonionic surfactant whose solubility in water increases sharply over 40° C., but which precipitates as a solid when the surfactant aqueous solution returns to normal temperature after dissolution.

Specific favorable examples of the specific surfactant include sucrose fatty acid esters (such as sucrose monostearic acid ester, sucrose monopalmiitic acid ester, sucrose monolauric acid ester, sucrose monooleic acid ester, sucrose distearic acid ester, sucrose dipalmitic acid ester, sucrose dilauric acid ester, sucrose dioleic acid ester, and sucrose coconut oil fatty acid ester) and polyglycerol fatty acid esters (such as polyglycerol monostearic acid ester and polyglycerol monooleic acid ester).

The amount in which the specific surfactant is contained in this emulsified composition is preferably 0.5 to 6 weight % of the composition, with 1 to 3 weight % being particularly favorable. If the content is less than 0.5 weight % of the composition, the oil component will tend not to bring out luster satisfactorily, but if the content is over 6 weight %, the surfactant will be prone to precipitation, which can cause problems in the usability of the product.

This emulsified composition can contain another surfactant (such as a nonionic surfactant other than the specific surfactant, an amphoteric surfactant, an anionic surfactant, or a cationic surfactant) in addition to the specific surfactant, but the desired effect of the present invention can be achieved even if substantially no other surfactant is contained. The phrase "substantially no other surfactant is contained" here means that no substance commonly used as a surfactant is contained, but does not prevent components that may have a slight surfactant effect from being contained.

The oil component is any common oil component that can be used in hair or skin cosmetics. Examples include liquid paraffin, squalane, and other such hydrocarbon oils, mink oil, jojoba oil, avocado oil, and other such animal and vegetable oils, cetyl isooctanoate, isopropyl myristate, isocetyl myristate, and other such ester oils, cetyl alcohol, isostearyl alcohol, behenyl alcohol, and other such higher alcohols, and stearic acid, palmitic acid, behenic acid, and other such higher fatty acids.

Other examples include dimethylpolysiloxane, methylphenylpolysiloxane, cyclic dimethylpolysiloxane, polyether-modified silicone, amino-modified silicone, betaine-modified silicone, alkyl-modified silicone, alkoxy-modified silicone, and other such silicone oils.

Of these, it is preferable for a silicone oil to be used as all or part of the oil component.

It is preferable for the amount in which the oil component is contained in this emulsified composition to be at least 3 weight % with respect to the composition, and to be no more than 10 parts to 1 part (weight ratio) of the specific surfactant. If the oil component content is less than 3 weight % with respect to the composition, the oil component will tend not to bring out luster satisfactorily, but if the content is over 10 parts to 1 part of the specific surfactant, it will be difficult to achieve an emulsified particle size of 0.5 μm or less.

It is preferable for the amount of water contained in this emulsified composition to be about 50 to 70 weight % with respect to the composition.

This emulsified composition can contain as needed any ordinary components commonly used in hair or skin cosmetics, in addition to the essential components discussed above. Specifically, a thickener, perfume, preservative, polyhydric alcohol, UV blocker, antioxidant, various kinds of medicinal component, and so forth can be added.

This emulsified composition is an oil-in-water emulsified composition, and its emulsified particles must be microparticles with an average size of 0.5 μm or less. If this average emulsified particle size is over 0.5 μm, the emulsified particles will be prone to crumbling, and when this emulsified composition is used on the hair, it will tend not to provide such long-lasting luster. There are no particular restrictions on the lower limit to the average size of these emulsified particles, but it is preferable for them to be as small as possible. However, even if a physical means for producing micro-emulsified particles is used, such as a high-pressure emulsification treatment (discussed below), the use of a surfactant in at least a commonly accepted amount will be necessary to achieve an average particle size of less than 0.01 μm. Thus, it is preferable for the lower limit to the average particle size of this emulsified composition to be about 0.01 μm. If it is desired to further reduce the amount of surfactant added, it is preferable for the lower limit to the average particle size to be about 0.1 μm.

Thus making the emulsified particles microparticles prevents precipitation of the specific surfactant when it is allowed to stand at normal temperature, and stabilizes the emulsified particles, and as a result, using this emulsified composition will impart luster to the hair for a longer period.

As a result of using micro-emulsified particles in this emulsified composition, the total surface area of the emulsified particles in the composition is greater and a larger portion of the specific surfactant is adsorbed at the oil-water interface, and this minimizes the aggregation of emulsified particles that can occur when the continuous phase (water) volatilizes. The result is that in the coating of the hair with this emulsified composition, all of the oil component is prevented from spreading over the hair right away, and instead the oil component is released gradually from the emulsified particles, will allows luster to be imparted for a longer period. Also, when the hair is touched with the hands or brushed, the emulsified particles readily break apart, and the oil component is released from the emulsified particles, so luster can be imparted whenever desired.

There are no particular restrictions on how the micro-emulsified particles are produced, but emulsified particles of the desired small size can usually be obtained by performing a high-pressure emulsification treatment. The desired fine emulsified particles can also be obtained by a microemulsion process or the like. There are no particular restrictions on the emulsification method, either, as long as the method allows an oil-in-water emulsified composition to be manufactured.

Typically, and preferably, for example, the oil component and water are pre-emulsified, after which micro-emulsified particles are produced by a high-pressure emulsification treatment or the like, and an oil phase component that has undergone a micro-sizing treatment is added to and dispersed in the aqueous phase component, which yields this emulsified composition.

This emulsified composition is an emulsified composition for hair, and can be used, for example, in the form of any hair cosmetic normally available on the market, such as a liquid, a gel, a cream, a lotion, an aerosol mist, or an aerosol foam.

The present invention provides an emulsified composition for hair, capable of imparting long-lasting luster.

Second Invention

It is preferable for the amount of hard surfactant contained in the first emulsified composition to be 0.5 to 6 weight % of the product content, with 1 to 3 weight % being particularly favorable.

The first emulsified composition can contain another surfactant (such as a nonionic surfactant other than a hard specific surfactant, an amphoteric surfactant, an anionic surfactant, or a cationic surfactant) in addition to the hard surfactant, but the targeted first emulsified composition can be manufactured even if substantially no other surfactant is contained.

The oil component is any common oil component that can be used in hair or skin cosmetics. Examples include liquid paraffin, squalane, and other such hydrocarbon oils, mink oil, jojoba oil, avocado oil, and other such animal and vegetable oils, cetyl isooctanoate, isopropyl myristate, isocetyl myristate, and other such ester oils, cetyl alcohol, isostearyl alcohol, behenyl alcohol, and other such higher alcohols, and stearic acid, palmitic acid, behenic acid, and other such higher fatty acids. Examples of the silicone oil used in the present invention include dimethylpolysiloxane, methylphenylpolysiloxane, cyclic dimethylpolysiloxane, polyether-modified silicone, amino-modified silicone, betaine-modified silicone, alkyl-modified silicone, alkoxy-modified silicone, and other such silicone oils.

Of these, it is preferable for a silicone oil to be used as all or part of the oil component.

It is preferable for the amount in which the oil component is contained in the first emulsified composition to be at least 3 weight % of the product content, and to be no more than 10 parts to 1 part (weight ratio) of the hard surfactant. If the oil component content is less than 3 weight % with respect to the product content, the oil component will tend not to bring out luster satisfactorily, but if the content is over 10 parts to 1 part of the hard surfactant, it will be difficult to achieve an emulsified particle size of 0.5 μm or less.

As discussed above, the first emulsified composition is an oil-in-water emulsified composition, and the emulsified particles (hard oil phase) thereof must consist of fine particles with an average size of 0-5 μm or less. If this average emulsified particle size is over 0.5 μm, the emulsified particles will be prone to crumbling, and when this emulsified composition is used on the hair, it will tend not to provide such long-lasting luster. There are no particular restrictions on the lower limit to the average size of these emulsified particles, but it is preferable for them to be as small as possible. However, even if a physical means for producing micro-emulsified particles is used, such as a high-pressure emulsification treatment, the use of a surfactant in at least a commonly accepted amount will be necessary to achieve an average particle size of less than 0.01 μm. Thus, it is preferable for the lower limit to the average particle size of the first emulsified composition to be about 0.01 μm. If it is desired to further reduce the amount of surfactant added, it is preferable for the lower limit to the average particle size to be about 0.1 μm.

There are no particular restrictions on how the hard oil phase is reduced to micro-size, but particles of the hard oil phase of the desired small size can usually be obtained by performing a high-pressure emulsification treatment. The desired fine emulsified particles can also be obtained by a microemulsion process or the like.

There are no particular restrictions on the emulsification method, either, as long as the method allows an oil-in-water emulsified composition to be manufactured. For example, the oil phase component containing the hard surfactant is mixed with water and pre-emulsified, after which micro-emulsified particles are produced by a high-pressure emulsification treatment or the like, and the product of the above microsizing treatment is added to and dispersed in the aqueous component, which yields the first emulsified composition.

Second Emulsified Composition

The second emulsified composition is an oil-in-water emulsified composition containing the following (d) to (f) and having an average emulsified particle size of 0.5 to 100 μm.

(d) a surfactant and/or an alkyl--modified carboxyvinyl polymer (e) an oil component (f) water The surfactant can be either a nonionic surfactant, an amphoteric surfactant, an anionic surfactant, or a cationic surfactant, but a nonionic surfactant is preferred.

Examples of nonionic surfactants include POE sorbitan monooleate, POE sorbitan monostearate, POE sorbitan tetraoleate, and other such POE sorbitan fatty acid esters; POE sorbitol monolaurate, POE sorbitol monooleate, POE sorbitol pentaoleate, POE sorbitol monostearate, and other such POE sorbitol fatty acid esters; POE glycerol monostearate, POE glycerol monoisostearate, POE glycerol triisostearate, and other such POE glycerol fatty acid esters; POE monooleate, POE distearate, POE dioleate, ethylene glycol distearate, and other such POE fatty acid esters; POE lauryl ether, POE oleyl ether, POE stearyl ether, POE behenyl ether, POE 2-octyl dodecyl ether, POE cholestanol ether, and other such POE alkyl ethers; POE octyl phenyl ether, POE nonyl phenyl ether, POE dinonyl phenyl ether, and other such PEO alkyl phenyl ethers; POE/POP-cetyl ether, POE/POP-2-decyl tetradecyl ether, POE/POP-monobutyl ether, POE/POP-lanolin hydrogenated, and POE/POP-glycerol ether, and other such POE/POP-alkylethers; tetronic and other such tetra POE/tetra POP-ethylenedimaine condensates; POE castor oil, POE hydrogenated castor oil, POE hydrogenated castor oil monoisostearate, POE hydrogenated castor oil triisostearate, POE hydrogenated castor oil monopyroglutamic monoisostearic diester, POE hydrogenated castor oil maleic acid, and other such POE castor oil or hydrogenated castor oil derivatives; POE sorbitol beeswax and other such POE beeswax/lanolin derivatives; coconut oil fatty acid diethanol amide, lauric acid monoethanolamide, fatty acid isopropanol amide, and other such alkanol amides; and POE propylene glycol fatty acid esters, POE alkylamines, POE fatty acid amides, PEO nonylphenylformaldehyde condensates, alkyl ethoxydimethylamine oxides, trioleyl phosphoric acid, and other such hydrophilic nonionic surfactants.

Of these nonionic surfactants, it is particularly favorable to use a POE hydrogenated castor oil derivative.

The amount in which the surfactant is contained in the second emulsified composition is preferably 0.01 to 5 weight % of the product content, with 0.1 to 3 weight % being particularly favorable.

An alkyl-modified carboxyvinyl polymer can also be used as the emulsifier of the second emulsified composition. An alkyl-modified carboxyvinyl polymer can be produced, or a commercially available product can be used. Examples of commercially available products include Carbopol 1342, Pemulen TR-1, and Pemulen TR-2 (all made by B.F. Goodrich Chemical).

The amount in which the alkyl-modified carboxyvinyl polymer is contained in the second emulsified composition is preferably 0.01 to 2 weight % of the product content, with 0.05 to 1 weight % being particularly favorable. The surfactant and the alkyl-modified carboxyvinyl polymer can be used individually in the second emulsified composition, or a combination thereof can be used.

The oil component of the second emulsified composition can be any ordinary oil component used in hair and skin cosmetics, just as with the oil component used in the above-mentioned first emulsified composition. Specific examples include liquid paraffin, squalane, and other such hydrocarbon oils, mink oil, jojoba oil, avocado oil, and other such animal and vegetable oils, cetyl isooctanoate, isopropyl myristate, isocetyl myristate, and other such ester oils, cetyl alcohol, isostearyl alcohol, behenyl alcohol, and other such higher alcohols, and stearic acid, palmitic acid, behenic acid, and other such higher fatty acids.

Other examples of the oil component in the second emulsified composition include dimethylpolysiloxane, methylphenylpolysiloxane, cyclic dimethylpolysiloxane, polyether-modified silicone, amino-modified silicone, betaine-modified silicone, alkyl-modified silicone, alkoxy-modified silicone, and other such silicone oils.

Of these, it is preferable for a silicone oil to be used as all or part of the oil component.

The second emulsified composition can be prepared by any standard procedure employed in the preparation of oil-in-water emulsified compositions. Specifically, the second emulsified composition can be prepared by using an emulsifier-in-water method, an alternating addition method, or the like.

As discussed above, the second emulsified composition is an oil-in-water emulsified composition, and the emulsified particles (soft oil phase) thereof must consist of particles with an average size of 0.5 to 100 μm. If this average emulsified particle size is below 0.5 μm, the product will tend not to provide as much luster immediately after use, but if 100 μm is exceeded, the stability of the emulsified particles will tend to be lost.

This Emulsified Composition

This emulsified composition, as discussed above, is an emulsified composition for hair, in which a hard oil phase (first emulsified composition) and a soft oil phase (second emulsified composition) are both present in an aqueous phase.

Thus, this emulsified composition can be manufactured simply by mixing the first emulsified composition and the second emulsified composition. As the proportion of hard oil phase in this emulsified composition is increased, the more emphasis will be on the setting strength of the hair product, and as the proportion of soft oil phase is increased, the emphasis will tend to be on the feel of the hair immediately after the hair product is used. These tendencies are taken into account in selecting the proportions in which the hard oil phase and soft oil phase are present in this emulsified composition, but generally, the oil component content in each phase is about 1:10 to 10:1 (hard oil phase:soft oil phase) as a weight ratio, with 1:4 to 4:1 being particularly favorable. The proportions of the aqueous phase and oil phase in this emulsified composition are also selected as dictated by the specific formulation of the final product, but generally, the weight ratio is about 20:1 to 3:1 (aqueous phase:oil phase).

In terms of manufacturing efficiency, it is preferable for this emulsified composition to be manufactured by using the full aqueous phase component of one emulsified composition, and adding to this the other oil phase component in which the aqueous phase component has been simplified and reduced in quantity. When this manufacturing method is employed, preparing the second emulsified composition containing the soft oil phase, and admixing the first emulsified composition, in which the aqueous phase has been simplified and reduced in quantity, to this second emulsified composition is favorable because the hard oil phase in the first emulsified composition is tougher, less apt to crumble, and easier to handle than the soft oil phase. More specifically, it is preferable for an emulsified composition consisting mainly of the hard oil phase, prepared by performing high-pressure emulsification or another such microemulsification process after pre-emulsion, to be mixed with a separately prepared second emulsified composition.

This emulsified composition can contain as needed any ordinary components commonly used in hair or skin cosmetics, in addition to the essential components discussed above. Specifically, a thickener, perfume, preservative, polyhydric alcohol, UV blocker, antioxidant, various kinds of medicinal component, and so forth can be added. Of these ordinary components, oil-based components can be enveloped as needed in the hard oil phase and/or the soft oil phase. As to water-based components, this emulsified composition can be manufactured by enveloping the aqueous phases of both the first emulsified composition and the second emulsified composition, or the aqueous phase of either one of these emulsified compositions, but as mentioned above, it is usually more efficient for the water-based component to be enveloped mainly in the aqueous phase of the second emulsified composition.

When this emulsified composition is used on the hair, the oil phase component in the soft oil phase is released immediately after use, imparting moisture and luster to the hair right away, and then as time passes, the oil phase component in the hard oil phase is gradually released, so that moisture and luster are imparted to the hair over time as well, which allows the hair to be set.

This emulsified composition is an emulsified composition for hair, and can be used, for example, in the form of any hair cosmetic normally available on the market, such as a liquid, a gel, a cream, a lotion, an aerosol mist, or an aerosol foam.

Examples of the present invention will now be discussed, but the present invention is not limited to or by these. Unless otherwise specified, all added amounts and contents are in weight percent.

FIRST INVENTION

Test Example 1

Examining the Manufacturing Method (Emulsified Particle Size)

Two types of emulsified composition (Example 1 and Comparative Example 1) were prepared from the following ingredients but by different methods.

| Added component | Added amount (weight %) |
| --- | --- |
| (A) | |
| purified water | balance |
| ethyl alcohol | 10 |
| carboxyvinyl polymer* | 0.35 |
| potassium hydroxide | 0.2 |
| perfume | as needed |
| preservative (paraben) | 0.1 |
| (B) | |
| dynamite glycerol | 1.6 |
| dipropylene glycol | 3.2 |

-continued

| Added component | Added amount (weight %) |
|---|---|
| sucrose fatty acid ester** | 2.0 |
| dimethylpolysiloxane (6 mPa · s) | 10 |
| purified water | small amount |

*Synthalen L (made by Wako Pure Chemical)
**DK Ester S-160 (made by Dai-ichi Kogyo Seiyaku)

Process 1: Except for the dimethylpolysiloxane, the ingredients in (B) were dissolved at 70° C., the dimethylpolysiloxane was mixed with this product, and pre-emulsification was performed, and then a high-pressure emulsification treatment was performed with an APV Gaulin (made by APV). Next, the (B) ingredients that had undergone the above-mentioned high-pressure emulsification treatment were added to and mixed with the mixed (A) ingredients to prepare a gelled emulsified composition (hair cream) (Example 1). The emulsified particle size of this hair cream was 0.3 μm.

Process 2: Except for the dimethylpolysiloxane, the ingredients in (B) were dissolved at 70° C., the dimethylpolysiloxane was mixed with this product, and pre-emulsification was performed, and then an ordinary emulsification treatment was performed with a homomixer. Next, the (B) ingredients that had undergone the above-mentioned emulsification treatment were added to and mixed with the mixed (A) ingredients to prepare a gel-form emulsified composition (hair cream) (Comparative Example 1).

Results: The above emulsified compositions were examined visually, which revealed that the emulsified composition of Example 1 was in the form of a turbid gel, whereas with the emulsified composition of Comparative Example 1, crystals of the surfactant precipitated and the composition solidified.

Test Example 2

Examining the Type of Surfactant

Using the following ingredients, two types of gelled emulsified composition (hair cream; Examples 1 and 2 and Comparative Example 2) containing different surfactants were prepared, following in every case the same preparation method as in. Process 1 in Test Example 1 above. The emulsified particle size of the hair creams of Examples 2 and 3 was 0.3 μm.

| Added component | Added amount (weihgt %) |
|---|---|
| (A) | |
| purified water | balance |
| ethyl alcohol | 10 |
| carboxyvinyl polymer* | 0.35 |
| potassium hydroxide | 0.2 |
| perfume | as needed |
| preservative (paraben) | 0.1 |
| (B) | |
| dynamite glycerol | 1.6 |
| dipropylene glycol | 3.2 |
| surfactant** | 2.0 |
| dimethylpolysiloxane (6 mPa · s) | 10 |
| purified water | small amount |

*Synthalen L (made by Wako Pure Chemical)
**Surfactant:

Example 2

Sucrose Monostearic Acid Ester (DK Ester 3-160)

Example 3

Polyglycerol Fatty Acid Ester (Glyceryl Stearate 10)

Comparative Example 2

POE (60) Hydrogenated Castor Oil

Results: The hair creams of Examples 2 and 3 and Comparative Example 2 above were applied to the hair of ten male and female test subjects, luster was brought out by combing the hair, and then the luster was examined visually four hours later and evaluated as follows.

Evaluation Criteria

Luster noted after elapsed time: at least nine of the test subjects noted luster comparable to that at the time of combing.

Luster not noted after elapsed time: fewer than nine of the test subjects noted luster comparable to that at the time of combing.

As a result, luster was noted after the elapsed time with the hair creams of Examples 2 and 3, but was not noted with the hair cream of Comparative Example 2.

It is clear from the results of Test Examples 1 and 2 that it is possible to provide an emulsified composition for hair with which luster is noted after elapsed time if a sucrose fatty acid ester or a polyglycerol fatty acid ester is used as the surfactant, and the average emulsified particle size is adjusted to between 0.1 and 0.5 μm by a high-pressure emulsification treatment.

Further, when this emulsified composition was prepared from the following ingredients and subjected to test 2 above, hair luster was noted after the elapsed time in all of the following Examples.

Example 4

Hair Foam

| Added component | Added amount (weight %) |
|---|---|
| (stock solution) | |
| (A) | |
| purified water | balance |
| ethyl alcohol | 10 |
| perfume | as needed |
| paraben | 0.1 |
| (B) | |
| dynamite glycerol | 1.6 |
| dipropylene glycol | 3.2 |
| sucrose fatty acid ester* | 2.0 |
| dimethylpolysiloxane (6 mPa · s) | 10 |
| (filler) | |
| stock solution | 90 |
| liquefied petroleum gas | 10 |

*DK Ester S-160 (made by Dai-ichi Kogyo Seiyaku)

Manufacturing Method

The (B) ingredients were mixed and pre-emulsified, after which this mixture was subjected to high-pressure emulsification in a microfluidizer, into which the (A) ingredients were mixed to prepare a stock solution. The emulsified particle size of this stock solution was 0.3 μm.

Liquefied petroleum gas was mixed into this stock solution as a filler, to manufacture a hair foam.

Example 5

Hair Spray

| Added component | Added amount (weight %) |
|---|---|
| (stock solution) | |
| (A) | |
| purified water | balance |
| ethyl alcohol | 10 |
| perfume | as needed |
| paraben | 0.1 |
| (B) | |
| dynamite glycerol | 1.6 |
| dipropylene glycol | 3.2 |
| sucrose fatty acid ester* | 2.0 |
| dimethylpolysiloxane (6 mPa · s) | 10 |
| (filler) | |
| stock solution | 90 |
| dimethyl ether | 10 |

*DK Ester S-160 (made by Dai-ichi Kogyo Seiyaku)

Manufacturing Method

The (B) ingredients were pre-emulsified, after which this mixture was subjected to high-pressure emulsification in a microfluidizer, into which the (A) ingredients were mixed to prepare a stock solution. The emulsified particle size of this stock solution was 0.3 μm.

Dimethyl ether was mixed into this stock solution as a filler, to manufacture a hair spray.

Example 6

Hair Cream

| Added component | Added amount (weight %) |
|---|---|
| (A) | |
| purified water | balance |
| ethyl alcohol | 10 |
| carboxyvinyl polymer | 0.35 |
| potassium hydroxide | 0.2 |
| phenoxyethanol | as needed |
| trisodium edetate | as needed |
| polyoxyethylene/polyoxypropylene random polymer methyl ether | 1 |
| (B) | |
| glycerol | 2 |
| dipropylene glycol | 2 |
| diglycerol | 1 |
| sucrose fatty acid ester | 2 |
| dimethylpolysiloxane (6 mPa · s) | 10 |
| high-molecular weight dimethylpolysiloxane (degree of polymerization n = 5000 to 8000) | 1 |
| poly(oxyethylene/polyoxypropylene) methylpolysiloxane copolymer | 1 |
| purified water | small amount |

Manufacturing Method

Except for the dimethylpolysiloxane, high-molecular weight dimethylpolysiloxane, and poly(oxyethylene/polyoxypropylene) methylpolysiloxane copolymer, the (B) ingredients were dissolved at 70° C., this product was mixed with the high-molecular weight dimethylpolysiloxane, and poly(oxyethylene/polyoxypropylene) methylpolysiloxane copolymer, pre-emulsification was performed, and then a high-pressure emulsification treatment was performed with an APV Gaulin (made by APV). Next, the (B) ingredients that had undergone the above-mentioned high-pressure emulsification treatment were added to and mixed with the mixed (A) ingredients to prepare a gelled emulsified composition (hair cream). The emulsified particle size of this hair cream was 0.3 μm.

Second Invention

The present invention provides an emulsified composition for hair with which moisture and luster can be imparted to the hair both immediately after use and over time, and an emulsified composition for hair with which setting can be performed. Preferred embodiments of the present invention will now be described through examples, but the scope of the present invention is not limited by these examples.

Test Example

An evaluation of the present invention was conducted for the ingredients listed in Tables 1-1 and 1-2 below.

TABLE 1-1

| | Example 7 | Example 8 |
|---|---|---|
| 1. ion exchange water | balance | balance |
| 2. ethyl alcohol | 10 | 10 |
| 3. carboxyvinyl polymer | 0.5 | 0.5 |
| 4. potassium hydroxide | 0.25 | 0.35 |
| 5. perfume | 0.2 | 0.2 |
| 6. methylparaben | 0.1 | 0.1 |
| 7. dynamite glycerol | 1.6 | 1.6 |
| 8. dipropylene glycerol | 3.2 | 3.2 |
| 9. sucrose fatty acid ester | 2 | 2 |
| 10. dimethylpolysiloxane (6 mPa · s) | 10 | 10 |
| 11. dimethylpolysiloxane (20 mPa · s) | 5 | 5 |
| 12. polyoxyethylene hydrogenated castor oil (60OE) | 2 | — |
| 13. alkyl-modified carboxyvinyl polymer* | — | 0.2 |

*Made by B. F. Goodrich Chemical

TABLE 1-2

| | Comp. Ex. 3** | Comp. Ex. 4*** | Comp. Ex. 5*** |
|---|---|---|---|
| 1. ion exchange water | balance | balance | balance |
| 2. ethyl alcohol | 10 | 10 | 10 |
| 3. carboxyvinyl polymer | 0.5 | 0.5 | 0.5 |
| 4. potassium hydroxide | 0.25 | 0.25 | 0.35 |
| 5. perfume | 0.2 | 0.2 | 0.2 |
| 6. methylparaben | 0.1 | 0.1 | 0.1 |
| 7. dynamite glycerol | 1.6 | 1.6 | 1.6 |
| 8. dipropylene glycerol | 3.2 | 3.2 | 3.2 |
| 9. sucrose fatty acid ester | 2 | — | — |
| 10. dimethylpolysiloxane (6 mPa · s) | 10 | 10 | 10 |
| 11. dimethylpolysiloxane (20 mPa · s) | 5 | 5 | 5 |
| 12. polyoxyethylene hydrogenated castor oil (60OE) | — | 2 | — |
| 13. alkyl-modified carboxyvinyl polymer* | — | — | 0.2 |

*Made by B. F. Goodrich Chemical
**Only high-pressure emulsification
***No high-pressure emulsification Manufacturing Method Example 7

(A portion) 7, 8, 9, and part of 1 are dissolved at 70° C. This solution is mixed with 10 and subjected to a high-pressure emulsification treatment. (B portion) 3 is dissolved in 1, and this solution is added to and mixed with 2, in which 5 and 6 have been dissolved. 12 is dissolved in this solution and added along with part of 1, part of 8, and 11 that have been emulsified, after which 4 is added to increase the viscosity. The A portion is added to and mixed with this.

Example 8

(A portion) 7, 8, 9, and part of 1 are dissolved at 70° C. This solution is mixed with 10 and subjected to a high-pressure emulsification treatment. (B portion) 3 and 13 are dissolved in 1, and this solution is added to and mixed with 2, in which 5 and 6 have been dissolved. 11 is added to this solution and emulsified, and 4 is added to increase the viscosity. The A portion is added to and mixed with this.

Comparative Example 3

(A portion) 7, 8, 9, and part of 1 are dissolved at 70° C. This solution is mixed with 10 and subjected to a high-pressure emulsification treatment. (B portion) 3 is dissolved in 1, and this solution is added to and mixed with 2, in which 5 and 6 have been dissolved. 4 is added to increase the viscosity. The A portion is added to and mixed with this.

Comparative Example 4

3 is dissolved in 1, and this solution is added to and mixed with 2, in which 5 and 6 have been dissolved. 7 and 8 are added. 12 is dissolved in this solution and added along with part of 8, 10, and 11 that have been emulsified, after which 4 is added to increase the viscosity. The A portion is added to and mixed with this.

Comparative Example 5

3 and 13 are dissolved in 1, and this solution is added to and mixed with 2, in which 5 and 6 have been dissolved. 7 and 8 are added. 10 and 11 are added to this and emulsified, and 4 is added to increase the viscosity.

Test Method

The above three types of test product were each applied in an amount of 5 g to the hair of 16 test subjects (eight men and eight women), and actual use evaluations were conducted for 1) luster, lightness, and non-oiliness immediately after application, 2) luster and lightness immediately after application and combing, and 3) luster and lightness. 4 hours after application and combing.

Evaluation Method

Luster
  ⊚: at least 13 subjects decided there was luster
  ○: 11 to 12 subjects decided there was luster
  ○Δ: 7 to 10 subjects decided there was luster
  Δ: 5 or 6 subjects decided there was luster
  x: 4 or fewer subjects decided there was luster Lightness
  ⊚: at least 13 subjects decided there was lightness
  ○: 11 to 12 subjects decided there was lightness
  ○Δ: 7 to 10 subjects decided there was lightness
  Δ: 5 or 6 subjects decided there was lightness
  x: 4 or fewer subjects decided there was lightness Non-oiliness
  ⊚: at least 13 subjects decided there was no oiliness
  ○: 11 to 12 subjects decided there was no oiliness
  ○Δ: 7 to 10 subjects decided there was no oiliness
  Δ: 5 or 6 subjects decided there was no oiliness
  x: 4 or fewer subjects decided there was no oiliness Results The results of these tests are given in Table 2.

TABLE 2

| | Immediately after application | | | Immed. after running fingers through hair and combing | | 4 hours later | |
| --- | --- | --- | --- | --- | --- | --- | --- |
| | Luster | NonOiliness | Light-ness | Luster | Lightness | Luster | Light-ness |
| Ex. 1 | ⊚ | ⊚ | ○ | ⊚ | ○ | ⊚ | ○ |
| Ex. 2 | ⊚ | ⊚ | ○ | ⊚ | ○ | ⊚ | ○ |
| C.E. 3 | ○ | ⊚ | ○ | ⊚ | ○ | ○ | ○ |
| C.E. 4 | ⊚ | Δ | Δ | Δ | ○ | ○Δ | ○ |
| C.E. 5 | ⊚ | Δ | Δ | Δ | ○ | Δ | ○ |

[C.E.: Comparative Example]

As shown in Table 2, the present invention products (Examples 7 and 8) earned evaluations of non-oiliness and lightness comparable to those of Comparative Example 3, in which just a hard oil phase was used as the oil phase, and also had excellent luster immediately after application, and this luster was maintained to a certain extent after combing. It can also be seen that an excellent state was maintained after 4 hours had elapsed.

Compared to Comparative Examples 4 and 5, in which just a soft oil phase was used as the oil phase, the luster after combing was far superior, and it can be seen that the luster after 4 hours had elapsed was better than in Comparative Examples 4 and 5.

In this test, it can be seen that the present invention products have excellent usability both immediately after the product is used and over time.

Examples will now be given of different formulations of the present invention, but all of the hair cosmetics of these formulations exhibited usability, both immediately after use and over time, comparable to or better than that of the present invention products in the above test.

Example 9

Foamed Composition

| Added component | Added amount (weight %) |
| --- | --- |
| 1. dimethylpolysiloxane (20 mPa · s) | 5.0 |
| 2. high-polymerization dimethylpolysiloxane (deg. of polymerization: 8000, 20% volatile isoparaffin solution) | 10.0 |
| 3. ethanol | 5.0 |
| 4. concentrated glycerol | 2.0 |
| 5. propylene glycol | 3.0 |
| 6. dipropylene glycol | 1.5 |
| 7. POE (60) hydrogenated castor oil | 1.0 |
| 8. sucrose monostearic acid ester | 1.0 |
| 9. POE (20) cetyl ether | 0.2 |
| 10. methylparaben | 0.2 |
| 11. hydrolyzed oat protein solution | 0.1 |
| 12. octyl methoxycinnamate | 0.1 |
| 13. perfume | as needed |
| 14. ion exchange water | balance |

Manufacturing Method

(A portion) 1, 4, 6, 8, and part of 14 were heated and dissolved, and a high-pressure emulsification treatment was performed to obtain an emulsion with an average emulsified particle size of 0.1 μm.

(B portion) 2, 5, 7 (heated and dissolved), 9, 12, and a suitable amount of 14 were mixed in a homomixer to obtain an emulsion with an average emulsified particle size of 5 μm.

14 was added to 11, to which were added 10 and 13, which had been dissolved in 3. The B portion was added to this, after which the A portion was added and mixed.

A vessel was filled with 90 parts of the stock solution prepared in this manner and 10 parts LPG (0.43 MPa, 20° C.) which yielded a foamed emulsified composition for hair.

Example 10

Cream Composition

| Added component | Added amount (weight %) |
| --- | --- |
| 1. dimethylpolysiloxane (20 mPa · s) | 5.0 |
| 2. high-polymerization dimethylpolysiloxane (deg. of polymerization: 10,000, 20% volatile isoparaffin solution) | 8.0 |
| 3. ethanol | 15.0 |
| 4. concentrated glycerol | 1.0 |
| 5. 1,3-butylene glycol | 3.0 |
| 6. dipropylene glycol | 1.0 |
| 7. POE (100) hydrogenated castor oil | 1.0 |
| 8. sucrose monostearic acid ester | 0.5 |
| 9. carboxyvinyl polymer | 0.5 |
| 10. methylparaben | 0.2 |
| 11. colorant | as needed |
| 12. aminomethylpropanol | as needed |
| 13. perfume | as needed |
| 14. ion exchange water | balance |

Manufacturing Method

(A portion) Part of 1, 4, 6, 8, and part of 14 were heated and dissolved, and a high-pressure emulsification treatment was performed to obtain an emulsion with an average emulsified particle size of 0.05 μm.

(B portion) 1, 2, 5, 7 (heated and dissolved) 9, 12, and a suitable amount of 14 were mixed in a homomixer to obtain an emulsion with an average emulsified particle size of 2.5 μm.

9 was dissolved, 11 was added to 14, to which 10 and 13 were added after being dissolved in 3. The B portion was added to this, after which the A portion was added and mixed. 12 was then added to increase the viscosity and obtain a cream-form emulsified composition for hair.

Example 11

Cream Composition

| Added component | Added amount (weight %) |
| --- | --- |
| 1. dimethylpolysiloxane (20 mPa · s) | 8.0 |
| 2. high-molecular weight aminopropyl dimethicone (molecular weight approx. 1,000,000, 10% dimethylpolysiloxane solution) | 1.0 |
| 3. ethanol | 10.0 |
| 4. concentrated glycerol | 1.0 |
| 5. 1,3-butylene glycol | 1.5 |
| 6. dipropylene glycol | 1.5 |
| 7. sucrose monostearic acid ester | 0.8 |
| 8. alkyl-modified carboxyvinyl polymer | 0.2 |
| 9. carboxyvinyl polymer | 0.5 |
| 10. phenoxyethanol | 0.2 |
| 11. royal jelly extract | 0.2 |
| 12. aminomethylpropanol | as needed |
| 13. perfume | as needed |
| 14. ion exchange water | balance |

Manufacturing Method

(A portion) Part of 1, 4, 6, 7, and part of 14 were heated and dissolved, and a high-pressure emulsification treatment was performed to obtain an emulsion with an average emulsified particle size of 0.08 μm.

(B portion) 11 was added to 8 and 9 which had been dissolved in 14, and 1, 2, and 5 were added, after which the system was mixed in a homomixer to obtain an emulsion with an average emulsified particle size of 30 μm. To this were added 3 (dissolved in 10), 13, and the A portion, and 12 was added to increase the viscosity and obtain a cream-form emulsified composition for hair.

Example 12

Foamed Composition

| Added component | Added amount (weight %) |
| --- | --- |
| 1. liquid paraffin | 3.0 |
| 2. volatile isoparaffin | 2.0 |
| 3. high-polymerization dimethylpolysiloxane (deg. of polymerization: 10,000 | 2.0 |
| 4. oleic acid | 2.0 |
| 5. 2-undecyl-N,N,N-(hydroxyethylcarboxymethyl)-2-imidazoline sodium | 3.0 |
| 6. ethanol | 10.0 |
| 7. concentrated glycerol | 1.0 |
| 8. propylene glycol | 1.5 |
| 9. dipropylene glycol | 1.5 |
| 10. sucrose monostearic acid ester | 0.8 |
| 11. phenoxyethanol | 0.2 |
| 12. perfume | as needed |
| 13. ion exchange water | balance |

Manufacturing Method (A portion) 1, 7, 9, 10, and part of 13 were heated and dissolved, and a high-pressure emulsification treatment was performed to obtain an emulsion with an average emulsified particle size of 0.05 μm.

(B portion) 2, 3, and 4 were mixed, and 5, 8, and part of 13 were added and emulsified to obtain an emulsion with an average emulsified particle size of 5 μm.

11 and 12 were added to and mixed with a solution of the B portion and 6 in 13, and the A portion was added to this mixture.

A vessel was filled with 92 parts of the stock solution prepared in this manner and 8 parts LPG (0.39 MPa, 20° C.), which yielded a foamed emulsified composition for hair.

The invention claimed is:

1. An emulsified composition for hair comprising:
    (a) a first oil in water emulsified composition having an average particle size of 0.5 μm or less, said first oil in water emulsified composition comprising:
        (i) 1-3 wt % of sucrose monostearatic acid ester;
        (ii) a first oil component contained in an amount of no more than 10 parts to 1 part of component (a)(i) above; and
        (iii) water; and
    (b) a second oil in water emulsified composition having an average particle size of 0.5-100 μm, said second oil in water emulsified composition comprising:
        (i) 0.1-3 wt % of polyoxyethylene hydrogenated castor oil or 0.01-2 wt % of alkyl modified carboxyvinyl polymer;
        (ii) a second oil component contained in an amount of no more than 10 parts to 1 part of component (b)(i) above; and
        (iii) water.

* * * * *